United States Patent
Koyano et al.

(10) Patent No.: US 8,022,247 B2
(45) Date of Patent: Sep. 20, 2011

(54) PROCESS FOR PRODUCTION OF 2,3,4-TRIFLUORO-5-(IODO OR BROMO)-BENZOIC ACID

(75) Inventors: Hiroshi Koyano, Kamakura (JP); Hitoshi Iikura, Kamakura (JP); Yoshiaki Isshiki, Kamakura (JP); Yasunori Kohchi, Kamakura (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 505 days.

(21) Appl. No.: 11/887,843

(22) PCT Filed: Apr. 6, 2006

(86) PCT No.: PCT/JP2006/307310
§ 371 (c)(1),
(2), (4) Date: Dec. 5, 2008

(87) PCT Pub. No.: WO2006/109661
PCT Pub. Date: Oct. 19, 2006

(65) Prior Publication Data
US 2009/0209785 A1 Aug. 20, 2009

(30) Foreign Application Priority Data

Apr. 6, 2005 (JP) ................................. 2005-110207

(51) Int. Cl.
*C07C 63/00* (2006.01)
(52) U.S. Cl. ...................................................... 562/405
(58) Field of Classification Search .................. None
See application file for complete search history.

(56) References Cited

U.S. PATENT DOCUMENTS 4,780,468 A 10/1988 Bridges et al.

FOREIGN PATENT DOCUMENTS

| JP | 63-154642 | 6/1988 |
|---|---|---|
| JP | 64-066180 | 3/1989 |
| JP | 10-067706 | 3/1998 |
| JP | 11-080076 | 3/1999 |
| JP | 2000-239223 | 9/2000 |
| JP | 2002-543055 | 12/2002 |
| JP | 2003-012597 | 1/2003 |
| WO | 96/02512 | 2/1996 |
| WO | 99/01426 | 1/1999 |
| WO | 00/64856 | 11/2000 |

OTHER PUBLICATIONS

Mongin, et al., "Extensive Halogen Scrambling and Buttressing Effects Encountered upon Treatment of Oligobromoarenes with Bases," Eur. J. Org. Chem., 2001, pp. 2771-2777.
Lulinski et al., "The Direct Iodination of Arenes with Chromium(VI) Oxide as the Oxidant," Bull. Chem. Soc. Jpn., 1997, vol. 70, pp. 1665-1669.
Lulinski et al., "Iodination of Both Deactivated and Activated Arenes with Sodium Periodate or Sodium Iodate as the Oxidants," Bull. Chem. Soc. Jpn., 2000, vol. 73, pp. 951-956.
Lulinski et al., "Eco-friendly Oxidative Iodination of Various Arenes with a Urea-Hydrogen Peroxide Adduct (UHP) as the Oxidant," Synthesis, 2004, No. 3, pp. 441-445.
Groweiss, Amiram., "Use of Sodium Bromate for Aromatic Bromination: Research and Development." Organic Process Research and Development, 2000, vol. 4, No. 1, pp. 30-33.
Khan et'al., "Monobromation of Deactivated Active Rings Using Bromine, Mercuric Oxide and Strong Acid," J. Org. Chem., 1988, vol. 53, pp. 1799-1800.
Duan et al.,"A Convenient New Method for the Bromination of Deactivated Aromatic Compounds," Synlett, 1999, No. 8, pp. 1245-1246.
Lulinski et al. "Oxidative Iodination of Arenes with Magnesium(IV) Oxide or Potassium Permangante as the Oxidants," Bull. Chem. Soc. Jpn., 1999, vol. 72, pp. 115-120.
Skulski, "Organic Iodine(I, III and V) Chemistry: 10 Years of Development at the Medical University of Warsaw, Poland," vol. 5, pp. 1331-1371.

*Primary Examiner* — Sudhakar Katakam
(74) *Attorney, Agent, or Firm* — Morgan, Lewis & Bockius LLP (57) ABSTRACT

The invention provides a process for production of 2,3,4-trifluoro-5-(iodo or bromo)benzoic acid, the process comprising a halogenation step in which direct iodination or bromination of 2,3,4-trifluorobenzoic acid is performed with an iodinating agent or brominating agent in a reaction solvent in the presence of an oxidizing agent. According to the invention, there is provided a process for convenient production of 2,3,4-trifluoro-5-(iodo or bromo)benzoic acid in high yield and high purity in a highly regioselective manner.

17 Claims, 3 Drawing Sheets

PROCESS FOR PRODUCTION OF 2,3,4-TRIFLUORO-5-(IODO OR BROMO)-BENZOIC ACID

TECHNICAL FIELD

The present invention relates to a process for production of 2,3,4-trifluoro-5-(iodo or bromo)benzoic acid, or in other words, a process for production of 5-iodo- or 5-bromo-substituted 2,3,4-trifluorobenzoic acid.

BACKGROUND ART 2,3,4-Trifluoro-5-(iodo or bromo)benzoic acid is useful as a synthetic intermediate of drugs, agricultural chemicals and the like, and it is used as, for example, an important intermediate for production of the diphenylamines described in Patent document 1, which are particularly useful as anticancer agents.

2,3,4-Trifluoro-5-bromobenzoic acid is useful as, for example, a raw material for production of 5-bromo-3,4-difluoro-2-(4-iodo-2-methylphenylamino)benzoic acid, an important intermediate, and it can be converted to 5-bromo-3,4-difluoro-2-(4-iodo-2-methylphenylamino)benzoic acid by coupling with 2-amino-5-iodotoluene by reference to the method described in Patent document 1. 5-Bromo-3,4-difluoro-2-(4-iodo-2-methylphenylamino)benzoic acid can be converted to a phenylaminobenzhydroxamic acid derivative that is an anticancer agent by reference to the method described in Patent document 1.

On the other hand, 2,3,4-trifluoro-5-iodobenzoic acid is also useful as a raw material for production of 2,3,4-trifluoro-5-trifluoromethylbenzoic acid, which is an important intermediate in the synthesis of quinolone carboxylic acids that are useful as antimicrobial agents or antiviral agents. 2,3,4-trifluoro-5-trifluoromethylbenzoic acid can be converted to a quinolone carboxylic acid with a 6-trifluoromethyl group by reference to the method described in, for example, Patent document 2 or Patent document 3.

Examples of known processes for obtaining 2,3,4-trifluoro-5-iodobenzoic acid include: (i) a process in which a 2,3,4-trifluorobenzoic acid is used as a starting material and subjected to a multistep reaction (for example, 2,3,4-trifluorobenzoic acid is used as a raw material and subjected to the following three steps: nitration; reduction of the nitro groups to amino groups; and iodination by Sandmeyer reaction (Patent document 4)); and (ii) a process in which 2,3,4-trifluoro-1,5-diiodobenzene is treated with LDA and then reacted with carbon dioxide (Non-patent document 1).

An example of a known process for obtaining 2,3,4-trifluoro-5-bromobenzoic acid is: (iii) a process in which 1-bromo-2,3,4-trifluorobenzene is used as a starting material and subjected to reaction with carbon dioxide at −78° C. in the presence of base for carboxylation (Patent document 1).

Patent document 1: International Patent Publication No. WO 99/01426
Patent document 2: International Patent Publication No. WO 96/02512
Patent document 3: Japanese Patent Application Laid-Open SHO 64-66180
Patent document 4: Japanese Patent Publication No. 3573249
Non-patent document 1: Eur. J. Org. Chem. 2001, 2771-2777

DISCLOSURE OF THE INVENTION

Problem to be Solved by the Invention

Yet the process (i) above not only requires three steps, but also has a total yield of only 54%, while the process (ii) above has a total yield of 36%. Therefore, neither process is industrially advantageous, and more efficient synthesis processes have been desired. Moreover, the processes (ii) and (iii) above require severe low temperature conditions, and thus are in need of improvement from the standpoint of economic efficiency.

In addition, in most halogenation reactions that potentially produce isomers such as regioisomers, the target product and isomeric byproducts usually have similar physicochemical properties, and cannot be easily separated and purified. Consequently, a production process for obtaining the target compound in high purity in a convenient manner while minimizing production of isomeric byproducts has been a desired goal.

It is an object of the present invention to provide an industrially advantageous process for production of 2,3,4-trifluoro-5-(iodo or bromo)benzoic acid, and more specifically, a process for convenient production of 2,3,4-trifluoro-5-(iodo or bromo)benzoic acid in high yield and high purity in a highly regioselective manner.

Means for Solving the Problem

In order to achieve the object stated above, the invention provides a process for production of 2,3,4-trifluoro-5-(iodo or bromo)benzoic acid represented by general formula (I) below, the process comprising a halogenation step in which direct iodination or bromination of 2,3,4-trifluorobenzoic acid represented by formula (II) below is performed with an iodinating agent or brominating agent in a reaction solvent in the presence of an oxidizing agent. Using an iodinating agent or brominating agent as in this process, direct bromination or iodination of 2,3,4-trifluorobenzoic acid can be accomplished. Throughout the present specification, the phrase "direct iodination or bromination" means iodinating or brominating 2,3,4-trifluorobenzoic acid in a single step to yield 2,3,4-trifluoro-5-(iodo or bromo)benzoic acid.

[Chemical Formula 1]

[where X represents an iodine atom or bromine atom.]

According to the production process described above, it is possible to obtain the target compound (2,3,4-trifluoro-5-

(iodo or bromo)benzoic acid) in high yield, with a reaction conversion rate (proportion of the raw material consumed by the reaction) of 99% or greater.

Since 2,3,4-trifluorobenzoic acid, the raw material, has two sites capable of iodination or bromination, which are the 5- and 6-positions on the aromatic ring, two different regioisomers could be produced. However, the production process described above achieves iodination or bromination at the 5-position with remarkably high regioselectivity. Moreover, the target compound can be obtained at a purity (proportion of the target compound in the reaction product) of 98% or greater.

The production process also allows the target compound to be isolated in high yield and high purity in a simple manner by only an extraction procedure that includes no step of acid solvent neutralization, without the need of a purification step (recrystallization, distillation or the like).

The production process is therefore a highly advantageous production process from an industrial standpoint.

In the halogenation step, the reaction solvent preferably contains an inorganic protonic acid and/or organic acid, and more preferably it contains both an inorganic protonic acid and organic acid. When the reaction solvent contains an inorganic protonic acid and/or organic acid, at least a portion of the inorganic protonic acids is preferably sulfuric acid, and at least a portion of the organic acids is preferably acetic acid. Throughout the present specification, the terms "sulfuric acid" and "$H_2SO_4$" refer to concentrated sulfuric acid (aqueous sulfuric acid with a concentration of 90% or greater and preferably 96% or greater), unless otherwise specified.

In the halogenation step, the inorganic protonic acid and/or organic acid is preferably added to the reaction system before addition of 2,3,4-trifluorobenzoic acid represented by formula (II). By adding the inorganic protonic acid and/or organic acid to the reaction system before addition of 2,3,4-trifluorobenzoic acid, it will become possible to improve the reactivity, and thereby to produce 2,3,4-trifluoro-5-(iodo or bromo)benzoic acid in a higher yield and with higher regioselectivity, compared to the case where the addition is not conducted.

In the halogenation step, preferably the oxidizing agent and iodinating agent or the oxidizing agent and brominating agent are further added to the reaction system after initiation of the halogenation reaction, and more preferably they are added two or more times. The reaction in the halogenation step typically proceeds in a solid/liquid two-layer system, or in a two-layer system of two different liquids. In such a two-layer system, further addition of the oxidizing agent and iodinating agent or the oxidizing agent and brominating agent can improve the reaction efficiency, thereby allowing the high reaction conversion rate to be maintained with greater reproducibility even on an industrial scale, compared to the case where the addition is not conducted.

In the halogenation step, the iodination or bromination is preferably carried out in the copresence of an acid anhydride, where the acid anhydride is preferably a carboxylic anhydride or sulfonic anhydride (more preferably at least one selected from the group consisting of acetic anhydride, oxalic anhydride and maleic anhydride). Addition of such an acid anhydride will activate the iodination or bromination reaction.

The iodination or bromination may also be carried out in the copresence of a water scavenger. The water scavenger traps water present or produced in the reaction system, and it is believed that the trapping of water prevents reduction in activity of the oxidizing agent. The aforementioned acid anhydride may also be used as a water scavenger.

The oxidizing agent is preferably a metal oxide, more preferably a Mn oxide and/or Cr oxide, and even more preferably activated $MnO_2$ and/or a $MnO_4^-$ salt ($NaMnO_4$, $KMnO_4$ or the like). The iodinating agent is preferably molecular iodine ($I_2$) and/or an iodide anion-containing molecule (LiI, NaI, KI or the like), and more preferably $I_2$. The brominating agent is preferably molecular bromine ($Br_2$) and/or a bromide anion-containing molecule (LiBr, NaBr, KBr or the like), and more preferably $Br_2$. When using such an iodinating agent or brominating agent which is not an oxidizing agent, an oxidizing agent is also added. Alternatively, at least a portion of the iodinating agents or brominating agents may be an iodinating agent or brominating agent that functions also as an oxidizing agent, i.e. an iodinating agent or brominating agent that is also an oxidizing agent. As the iodinating agent that is also an oxidizing agent, there are preferred one or more selected from the group consisting of $NaIO_3$, $NaIO_4$, $KIO_3$ and $KIO_4$, and as the brominating agent that is also an oxidizing agent, there are preferred one or more selected from the group consisting of $NaBrO_3$, $NaBrO_4$, $KBrO_3$ and $KBrO_4$. The iodinating agents and brominating agents mentioned above are especially suitable for reactions wherein the substrate is 2,3,4-trifluorobenzoic acid, and their use can yield 2,3,4-trifluoro-5-(iodo or bromo)benzoic acid conveniently in high yield and high purity in a highly regioselective manner. When using such an iodinating agent or brominating agent which is also an oxidizing agent, a different oxidizing agent or a different iodinating agent or brominating agent may also be added.

The halogenation step is preferably followed by an extraction step in which the reaction mixture obtained from the halogenation step is added to water, and 2,3,4-trifluoro-5-(iodo or bromo)benzoic acid represented by general formula (I) is then extracted with an organic solvent. The water used here is preferably neutral (pH: 6 to 8) ice water.

The reaction mixture obtained in the halogenation step may be added to water (ice water) for completion of the reaction, lowering of the liquid temperature, extraction of components, or the like. If the water (ice water) is rendered non-basic (preferably neutral (pH: 6 to 8)), it is possible to more easily prevent generation of heat of neutralization and migration of the target carboxylic acid (2,3,4-trifluoro-5-(iodo or bromo)benzoic acid) into the aqueous layer, as compared to addition to ice water containing NaOH, $(NH_4)_2CO_3$, $Na_2SO_3$, $Na_2S_2O_3$ or the like, and this can provide significant industrial advantages.

According to this production process, it is possible to obtain 2,3,4-trifluoro-5-(iodo or bromo)benzoic acid represented by general formula (I) at a purity of 98% or greater without purification after the halogenation step.

On the other hand, many different processes are known for iodination or bromination of a hydrogen atom on the aromatic ring of an aromatic compound, and the following processes have been reported for direct (single-step) iodination or bromination of an electron-deficient aryl compound that is free of an electron-donating group such as a phenolic hydroxyl group and have an electron-withdrawing group such as a carboxyl group.

1) Iodination using Cr (Bull. Chem. Soc. Jpn. 1997, 70, 1665-1669)
2) Iodination using Mn (Bull. Chem. Soc. Jpn. 1999, 72, 115-120)
3) Iodination using $NaIO_4$ or $NaIO_3$ (Bull. Chem. Soc. Jpn. 2000, 73, 951-956)

4) Iodination using $H_2O_2$ (Synthesis 2004, 441-445)

5) Bromination using $NaBrO_3$ (Organic Process Research and Development 2000, 4, 30-33)

6) Bromination using $H_2O_2$ (Japanese Patent Application Laid-Open SHO 63-171452)

7) Bromination using Hg (Journal of Organic Chemistry 1988, 53, 1799)

8) Bromination using NBS (Synlett 1999, 1245)

However, none of the aforementioned publications describe the use of 2,3,4-trifluorobenzoic acid as a raw material. Moreover, they do not mention the use of aryl compounds such as 2,3,4-trifluorobenzoic acid, i.e. aryl compounds having three or more bonded functional groups of different orientations or aryl compounds with extremely low reactivity having three or more bonded electron-withdrawing groups, nor do they describe or suggest a process for direct iodination or bromination of such aryl compounds. In other words, the prior art has not demonstrated high reactivity in direct halogenation of 2,3,4-trifluorobenzoic acid, which has both a carboxyl group (one) and fluoro groups (three) as inactive groups, nor regioselectivity of the halogenation. The present inventors have been the first to discover that the halogenation step described above can produce 2,3,4-trifluoro-5-(iodo or bromo)benzoic acid in high yield and high purity in a highly regioselective manner.

Effects of the Invention

According to the invention, there is provided a process for convenient production of 2,3,4-trifluoro-5-(iodo or bromo) benzoic acid in high yield and high purity in a highly regioselective manner.

BEST MODES FOR CARRYING OUT THE INVENTION

Preferred embodiments of the invention will now be explained.

The production process of the invention is a process for production of 2,3,4-trifluoro-5-(iodo or bromo)benzoic acid represented by general formula (I) below, the process comprising a halogenation step in which direct iodination or bromination of the 5-position of 2,3,4-trifluorobenzoic acid represented by formula (II) below is performed with an iodinating agent or brominating agent in a reaction solvent in the presence of an oxidizing agent.

[Chemical Formula 2]

(I)

(II)

[where X represents an iodine atom or bromine atom.]

As the iodinating agent and brominating agent, there may be mentioned $I_2$ and $Br_2$, as well as anionic species (compounds containing iodide anion or bromide anion) such as LiI, LiBr, NaI, NaBr, KI and KBr, or radical or cationic species such as NBS and NIS. Also included are reagents exhibiting functions as both an oxidizing agent and halogenating agent, such as $HIO_3$, $HIO_4$, $LiIO_3$, $LiIO_4$, $NaIO_3$, $NaIO_4$, $KIO_3$, $KIO_4$, $LiBrO_3$, $LiBrO_4$, $NaBrO_3$, $NaBrO_4$, $KBrO_3$ and $KBrO_4$. Preferred are $I_2$, $Br_2$, NaI, NaBr, $NaIO_3$, $NaIO_4$, $KIO_3$, $KIO_4$, $NaBrO_3$, $NaBrO_4$, $KBrO_3$ and $KBrO_4$, and particularly preferred are $I_2$ and $Br_2$.

As the oxidizing agent, there may be mentioned metal oxides and peroxides, with metal oxides being preferred. When the iodinating agent or brominating agent used does not have an oxidizing action, an oxidizing agent is added in addition to the iodinating agent or brominating agent. NBS, NIS, $HIO_3$, $HIO_4$, $LiIO_3$, $LiIO_4$, $NaIO_3$, $NaIO_4$, $KIO_3$, $KIO_4$, $LiBrO_3$, $LiBrO_4$, $NaBrO_3$, $NaBrO_4$, $KBrO_3$, $KBrO_4$ and the like are believed to also function as an oxidizing agent in light of their reaction properties. Therefore, in the production process of the invention, their use is believed to promote direct halogenation even without addition of a separate oxidizing agent.

As the metal oxide, there may be mentioned activated $MnO_2$, $MnO_4^-$ salts ($NaMnO_4$, $KMnO_4$, etc.), $CrO_3$, $Cr_2O_7^{-2}$ salts ($K_2Cr_2O_7$, $Na_2Cr_2O_7$, $Li_2Cr_2O_7$, $(NH_4)_2Cr_2O_7$, etc.), $Pb(OAc)_4$ and the like, with activated $MnO_2$, $KMnO_4$ and $CrO_3$ being preferred, and activated $MnO_2$ being particularly preferred. Activated $MnO_2$ can be obtained, for example, by heating of $MnO_2$ under reduced pressure, where activation of the $MnO_2$ is thought to occur due to dehydration, surface area increase, etc.

The peroxide may be an organic peroxide or inorganic peroxide. As the organic peroxide, there may be mentioned $CH_3CO_3H$, $CH_2ClCO_3H$, $CHCl_2CO_3H$, $CCl_3CO_3H$, $CH_2FCO_3H$, $CHF_2CO_3H$, $CF_3CO_3H$, $PhCO_3H$ and the like, among which $CH_3CO_3H$, $CF_3CO_3H$ and $PhCO_3H$ are preferred. As the inorganic peroxide, there may be mentioned $H_2O_2$, urea-$H_2O_2$, $HIO_3$, $HIO_4$, $LiIO_3$, $LiIO_4$, $NaIO_3$, $NaIO_4$, $KIO_3$, $KIO_4$, $LiBrO_3$, $LiBrO_4$, $NaBrO_3$, $NaBrO_4$, $KBrO_3$, $KBrO_4$ and the like, among which $H_2O_2$, $NaIO_3$, $NaIO_4$, $KIO_3$, $KIO_4$, $NaBrO_3$, $NaBrO_4$, $KBrO_3$ and $KBrO_4$ are preferred. Of these inorganic peroxides, $HIO_3$, $HIO_4$, $LiIO_3$, $LiIO_4$, $NaIO_3$, $NaIO_4$, $KIO_3$, $KIO_4$, $LiBrO_3$, $LiBrO_4$, $NaBrO_3$, $NaBrO_4$, $KBrO_3$, $KBrO_4$ and the like also have a halogenating action, and can therefore also act as a halogenating agent. In addition to such a peroxide that also has a halogenating action, there may be simultaneously added a different halogenating agent such as $I_2$, $Br_2$, NaI or NaBr.

In the production process of the invention, an acid anhydride is preferably added. Preferred as the acid anhydride are carboxylic anhydrides represented by general formula (III) below, and sulfonic anhydrides represented by general formula (IV) below.

[Chemical Formula 3]

(III)

(IV)

[where R and R' each independently represent a $C_1$-$C_{10}$ alkyl or alkenyl group optionally substituted with F, Cl, Br or I. R and R' may also together form a $C_2$-$C_{10}$ alkylene chain, thereby forming a ring.]

As examples of such acid anhydrides, there may be mentioned acetic anhydride ($Ac_2O$), $(CH_3CH_2CO)_2O$, oxalic anhydride, maleic anhydride, $(CF_3CO)_2O$, $(CH_3SO_2)_2O$, $(CH_3CH_2SO_2)_2O$ and the like, among which carboxylic anhydrides are preferred and $Ac_2O$ is more preferred. The reason why it is preferred to add an acid anhydride in the production process of the invention is that addition thereof can prevent inactivation of the oxidizing agent by trace water. However, functions of the acid anhydride are not limited to this.

As the reaction solvent, there may be mentioned solvents containing an inorganic protonic acid or organic acid. As the inorganic protonic acid, there may be mentioned sulfuric acid ($H_2SO_4$), water ($H_2O$), phosphoric acid ($H_3PO_4$) and the like, and as the organic acid, there may be mentioned acetic acid (AcOH) and the like. Two or more different solvents may be used in admixture. For example, a mixture of an inorganic protonic acid (for example, $H_2SO_4$) and organic acid (for example, AcOH), or a mixture of two different inorganic protonic acids (for example, $H_2SO_4$ and $H_2O$) may be used. It is particularly preferred to use a mixture of an inorganic protonic acid and organic acid. The reaction solvent may or may not form part of the reaction system.

The amount of reaction solvent used is preferably 0.8 to 8.0 L with respect to 1 mol of 2,3,4-trifluorobenzoic acid, and for example, when a mixed solvent of AcOH and $H_2SO_4$ is used, the amounts of AcOH and $H_2SO_4$ are preferably 0.4 to 3.6 L and 0.5 to 4.5 L, respectively. If the amount of solvent is reduced, the reduced solubility will hamper stable uniform stirring of the reaction system, and therefore it is preferred to use at least 0.8 L of reaction solvent with respect to 1 mol of 2,3,4-trifluorobenzoic acid. Use of the solvent in an amount which is greater than the aforementioned range will not necessarily affect the progress of the reaction, but use of an excess of reaction solvent is not desirable in terms of economic efficiency. Moreover, for example, if the proportion of inorganic protonic acid such as $H_2SO_4$ is increased, the viscosity of the reaction system will be higher, and stirring may not be uniform. If stirring is uneven in the production process of the invention, especially with a solid-liquid two-layer system reaction, the reaction progress may be hindered. Therefore, the amount of reaction solvent used is preferably within the range specified above.

The amounts of acid anhydride and iodinating agent or brominating agent added are preferably 3 to 30 mol and 0.7 to 3 mol, respectively, with respect to 1 mol of 2,3,4-trifluorobenzoic acid. When the oxidizing agent is added separately from the iodinating agent or brominating agent, the amount thereof is preferably 1 to 10 mol with respect to 1 mol of 2,3,4-trifluorobenzoic acid.

As a preferred embodiment of the halogenation step, there may be mentioned one in which: (1) $I_2$ and $Br_2$ are used as the iodinating agent and brominating agent, respectively; (2) an acid anhydride ($Ac_2O$ or the like) is added; (3) activated $MnO_2$ is added as the oxidizing agent; and (4) a mixed solvent of AcOH and $H_2SO_4$ is added as the reaction solvent. This embodiment can be represented by the following reaction formula, for example.

[Chemical Formula 4]

As another preferred embodiment of the halogenation step, there may be mentioned one in which at least one of steps (a) and (b) below is carried out. In this embodiment, steps (a) and (b) are preferably followed by step (c) below, and more preferably step (c) is carried out two or more times. The iodinating agent and brominating agent used are preferably $I_2$ and $Br_2$, respectively. The mixture of the reaction solvent and acid anhydride used for step (a) is preferably obtained by, for example, adding the inorganic protonic acid to the mixture of the organic acid and acid anhydride.

(a) A step of adding the oxidizing agent and iodinating agent or the oxidizing agent and brominating agent to a mixture of the reaction solvent (containing an inorganic protonic acid and/or organic acid) and an acid anhydride (b) A step of adding 2,3,4-trifluorobenzoic acid to the mixture obtained from step (a)

(c) A step of adding the oxidizing agent and iodinating agent or the oxidizing agent and brominating agent to the mixture obtained from step (b)

In the halogenation step, when an iodinating agent or brominating agent that is also an oxidizing agent is used, it is also preferred to use a solvent composed solely of an inorganic protonic acid as the reaction solvent. In this case, the inorganic protonic acid used is preferably, for example, $H_2O$ or $H_2SO_4$.

The following factors 1) to 4) should be taken into account when carrying out the production process of the invention.

1) Heat is generated when $H_2SO_4$ is added to the solvent or solution. More specifically, the mixture will be nonuniform immediately after the addition of $H_2SO_4$, and excess heat will be generated at points where $H_2SO_4$ is present at high local concentration. When the reaction reagents (oxidizing agent and/or iodinating or brominating agent) and the reaction substrate (2,3,4-trifluorobenzoic acid) are already present in the reactor before the addition of $H_2SO_4$, the local heat generation may cause local and brief contact between the reaction substrate and reaction reagents at high temperature, creating a byproduct or increasing undesirable side reactions. Therefore, in the production process of the invention, the $H_2SO_4$ is preferably added before addition of the reaction substrate. When the $H_2SO_4$ is added, the temperature is not particularly restricted, but preferably it does not exceed the boiling points of the molecules composing the solvent or solution to be mixed with the $H_2SO_4$.

2) The temperature during addition of the iodinating or brominating agent after the addition of H₂SO₄ and the temperature during the subsequent iodination or bromination reaction are usually from room temperature to 100° C., but from the viewpoint of reaction acceleration and side reaction inhibition, it is preferably 40 to 90° C. and more preferably 40 to 60° C. The temperature may also be repeatedly increased in a stepwise fashion. In order to achieve satisfactory stirring efficiency, the iodinating or brominating agent and the oxidizing agent are preferably mixed in stages. The reaction time for the production process of the invention will normally be 2 to 7 hours, but when the mixing is carried out in stages, the reaction is preferably conducted over a period 2 to 15 times longer. The reaction pressure for the production process of the invention is not particularly restricted, but will normally be atmospheric pressure.

3) The following is a preferred example of a method for isolating 2,3,4-trifluoro-5-(iodo or bromo)benzoic acid, the target product of the invention. First, the reaction mixture is added to an ice bath. Here, in order to prevent generation of heat of neutralization, and in order to facilitate extraction of the target product, a carboxylic acid derivative, into the organic layer, the aqueous layer is preferably not a basic aqueous solution. The target compound is then extracted into the organic layer with an appropriate organic solvent. After washing the organic layer with an aqueous solution containing a reducing agent (Na₂S₂O₃ aqueous solution, Na₂SO₃ aqueous solution, or the like), the organic layer is dehydrated and concentrated to dryness for isolation.

4) The obtained crude 2,3,4-trifluoro-5-(iodo or bromo)benzoic acid may be purified by, for example, distillation, rinsing or recrystallization according to the intended purpose.

The compound obtained by the production process of the invention (2,3,4-trifluoro-5-(iodo or bromo)benzoic acid) can be utilized for production of, for example, 3,4-difluoro-2-(2-fluoro-4-iodophenylamino)-5-(formyl or vinyl)benzoic acid, 5-(formyl or vinyl)-3,4-difluoro-2-(4-iodo-2-methylphenylamino)benzoic acid and the like, which are synthetic intermediates of phenylaminobenzhydroxamic acid derivatives that are useful as drugs, especially as anticancer agents.

3,4-difluoro-2-(2-fluoro-4-iodophenylamino)-5-vinylbenzoic acid or 3,4-difluoro-2-(2-fluoro-4-iodophenylamino)-5-formylbenzoic acid can be produced by the process represented by the following reaction formula, for example. Each step of this production process will be explained below.

[Chemical Formula 5]

[where X represents an iodine atom or bromine atom.]

Step 1:

2,3,4-trifluoro-5-(iodo or bromo)benzoic acid (compound (1)), which is obtained by the production process of the invention, can be converted to 2,3,4-trifluoro-5-vinylbenzoic acid (compound (2)) by, for example, reaction with a vinylating organometallic reagent in the presence of a transition metal catalyst in an appropriate solvent. The reaction may be easily carried out by reference to a relevant literature (for example, J. K. Stille, Angew. Chem., Int. Ed. Engl. 1986, 25, 508-524; N. Miyaura, A. Suzuki, Chem. Rev. 1995, 95, 2457-2483; A. Suzuki, J. Organomet. Chem., 1999, 576, 147-168; Suzuki, A, In Metal-Catalyzed Cross Coupling Reactions, Diederich, F., Stang, P. J., Eds., VCH: Weinheim, 1998, pp. 49-97).

Step 2:

2,3,4-trifluoro-5-vinylbenzoic acid (compound (2)) can be converted to 3,4-difluoro-2-(2-fluoro-4-iodophenylamino)-5-vinylbenzoic acid (compound (4)) by coupling with 2-fluoro-4-iodoaniline (compound (3)). The reaction may be carried out, for example, using a method described in a relevant literature (for example, International Patent Publication No. WO 00/64856; M. H. Chen, V. G. Beylin, E. Iakovleva, S. J. Kesten, J. Magano, D. Drieze, Synthetic Communications, 32 (3), 411-417 (2002)), or by a similar method.

Step 3:

3,4-difluoro-2-(2-fluoro-4-iodophenylamino)-5-vinylbenzoic acid (compound (4)) can be converted to 3,4-difluoro-2-(2-fluoro-4-iodophenylamino)-5-formylbenzoic acid (compound (5)) by reaction with an appropriate oxidizing agent (for example, ozone, osmium tetroxide-sodium metaperiodate, or ruthenium chloride-sodium metaperiodate).

Step 4:

2,3,4-trifluoro-5-vinylbenzoic acid (compound (2)) can be converted to 2,3,4-trifluoro-5-formylbenzoic acid (compound (6)) by reaction with an appropriate oxidizing agent (for example, ozone, osmium tetroxide-sodium metaperiodate, or ruthenium chloride-sodium metaperiodate).

Step 5:

2,3,4-trifluoro-5-formylbenzoic acid (compound (6)) can be converted to 3,4-difluoro-2-(2-fluoro-4-iodophenylamino)-5-formylbenzoic acid (compound (5)) by coupling with 2-fluoro-4-iodoaniline (compound (3)). The reaction may be carried out, for example, using a method described in a relevant literature (for example, International Patent Publication No. WO 00/64856; M. H. Chen, V. G. Beylin, E. Iakovleva, S. J. Kesten, J. Magano, D. Drieze, Synthetic Communications, 32 (3), 411-417 (2002)), or by a similar method.

EXAMPLES

The present invention will now be explained in greater detail based on examples and comparative examples, with the understanding that the examples below are in no way limitative on the invention.

The raw material and reagents used in the examples are as follows.

2,3,4-Trifluorobenzoic acid: product of Oakwood Products, Inc., Catalog No. 1808, Lot No. H7988

AcOH: product of Wako Pure Chemical Industries, Ltd., Catalog No. 012-00245, Lot No. ASL7730

$Ac_2O$: product of Wako Pure Chemical Industries, Ltd., Catalog No. 011-00276, Lot No. ASL9439

$H_2SO_4$: product of Wako Pure Chemical Industries, Ltd., Catalog No. 192-04696, Lot No. KCQ7389

$Br_2$: product of Wako Pure Chemical Industries, Ltd., Catalog No. 024-02401, Lot No. CEQ7093

Activated $MnO_2$: product of Aldrich Co., Catalog No. 217646, Lot No. 09114AB, purity: 85%

The HPLC conditions for Example 1 are as follows.

Apparatus: 996-600E by Waters Corporation

Column: Combi ODS (ODS, 5 μm, 4.6 mm I.D.×50 mm, product of Wako Pure Chemical Industries, Ltd.), COSMO-SIL (ODS, 5 μm, 4.6 mm I.D.×50 mm, product of Nacalai Tesque, Inc.), or Inertsil C18 (ODS, 5 μm, 4.6 mm I.D.×50 mm, product of GL Sciences Inc.)

Mobile phase: Water containing 0.01% trifluoroacetic acid (A), and acetonitrile containing 0.01% trifluoroacetic acid (B)

Elution method: Stepwise solvent gradient elution (solvent composition changed from 10% B to 95% B over 3.5 minutes, followed by change to 10% B over 1 minute, and then maintaining 10% B for 0.5 minute.)

Flow rate: 4.0 mL/min

The HPLC conditions for Examples 2 and 3 are as follows.

Apparatus: LCMS2525ZQ by Waters Corporation

Column: SunFire (ODS, 5 μm, 4.6 mm I.D.×50 mm) by Waters Corporation

Mobile phase: Water containing 0.05% trifluoroacetic acid (A), and acetonitrile containing 0.05% trifluoroacetic acid (B)

Elution method: Stepwise solvent gradient elution (solvent composition changed from 10% B to 95% B over 3.5 minutes, followed by change to 10% B over 1 minute, and then maintaining 10% B for 5 minutes.)

Flow rate: 4.0 mL/min

Example 1

2,3,4-Trifluoro-5-iodobenzoic Acid

AcOH (1.2 L) and $Ac_2O$ (0.63 L) were added to a 5 L flask. $H_2SO_4$ (1.6 L) was then added to the same flask while cooling with ice to prevent the temperature from exceeding 40° C. Next, $I_2$ (70 g), activated $MnO_2$ (70 g) and 2,3,4-trifluorobenzoic acid (120 g, 0.68 mol) were added in solid form while stirring at room temperature. While stirring the resulting dark purple suspension at 50° C., $I_2$ (70 g) and activated $MnO_2$ (70 g) were added after 2 to 3 hours, and $I_2$ (33 g) and activated $MnO_2$ (37 g) were further added after 4 to 6 hours. After 24 hours, the reaction mixture was added to ice water (2 L). The purple organic layer obtained by extraction three times with $CH_2Cl_2$ (1.6 L, 1.0 L, 1.0 L) was washed twice with 0.2N $Na_2S_2O_3$ aqueous solution (2.0 L, 1.0 L), resulting in alteration of the organic layer color to pale yellow. The organic layer was washed four times with 1.0 L of water to remove the AcOH, yielding a non-cloudy transparent organic layer. After removing water in the organic layer with $Na_2SO_4$ (1.3 kg), the solvent was removed by distillation to yield 192 g of 2,3,4-trifluoro-5-iodobenzoic acid (0.64 mol, 94%, purity: 99 LC area % (UV peak area % in LC)) as white powders. If necessary, rinsing may be performed with a mixed solvent of ethanol and hexane (EtOAc: hexane=1:9 (v/v)).

Figure 1:
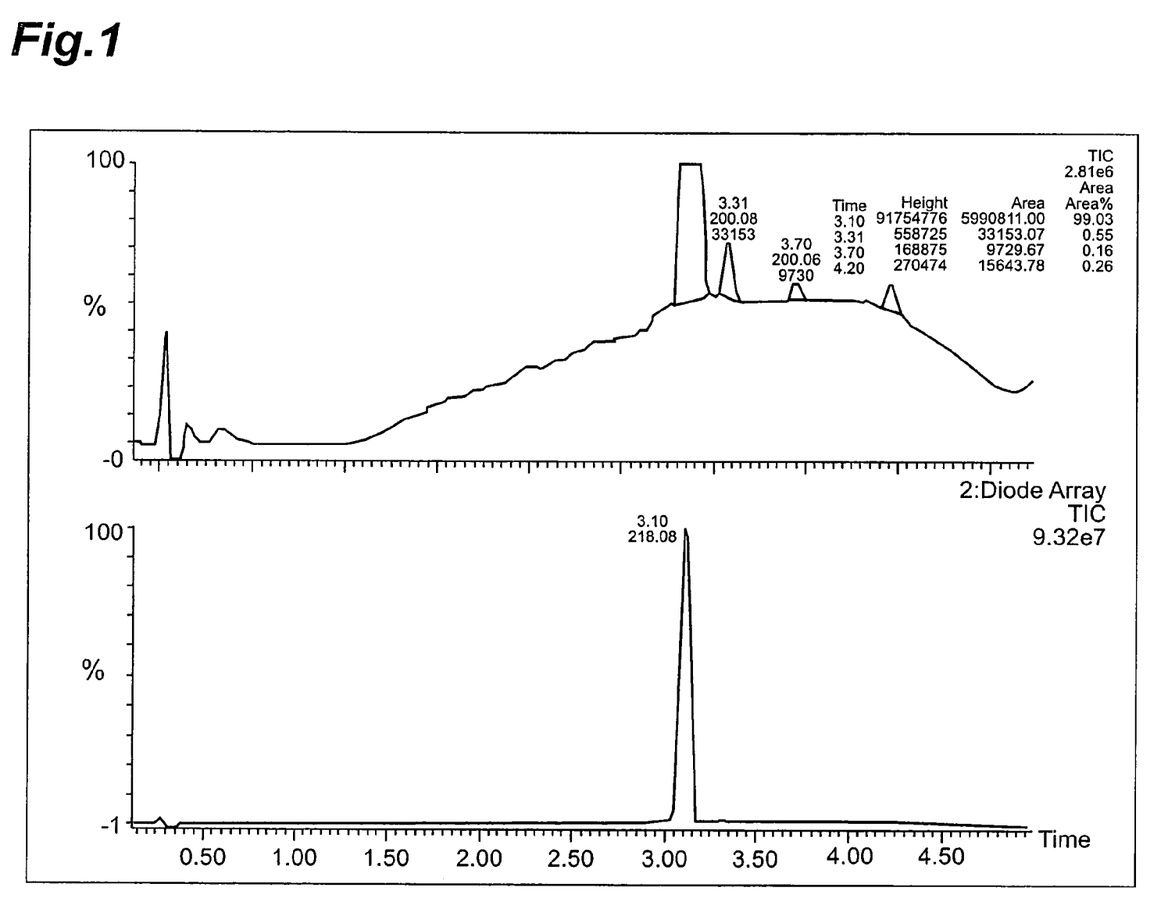
FIG. 1 is a chart from high performance liquid chromatography (HPLC) of the 2,3,4-trifluoro-5-iodobenzoic acid obtained in Example 1.

A chart from high performance liquid chromatography (HPLC) of the obtained 2,3,4-trifluoro-5-iodobenzoic acid is shown in FIG. 1. As seen in FIG. 1, the production process of the invention yields a high-purity target compound even without purification such as recrystallization. Specifically, the UV intensity of the target compound at 3.10 minutes was 99.03%, which is above the target purity of 98%. There were only three impurities with peak intensities smaller than 0.1% (3.31 minutes, 3.71 minutes, 4.20 minutes). This demonstrates that the production process of the invention yields 2,3,4-trifluoro-5-iodobenzoic acid in remarkably high purity and with remarkably high regioselectivity.

The instrumental analysis ($^1$H-NMR) data for the obtained 2,3,4-trifluoro-5-iodobenzoic acid is as follows.

$^1$H-NMR (CDCl$_3$, 270 MHz) δ (ppm): 8.25 (1H, ddd, J=6.9, 6.4, 2.5 Hz).

Example 2

2,3,4-Trifluoro-5-bromobenzoic Acid

The following reaction was conducted under a nitrogen atmosphere using a 300 mL three-necked round bottom flask equipped with a magnetic stirrer, internal thermometer (without compensation) and dropping funnel. An oil bath was used for heating.

AcOH (50 mL) and Ac$_2$O (27 mL) were placed in the flask and cooled using an ice bath. H$_2$SO$_4$ (67 mL) was added dropwise over a period of 20 minutes while controlling the dropping speed so that the internal temperature did not exceed 40° C. The ice bath was then removed and the reaction mixture was returned to room temperature, and then Br$_2$ (0.60 mL, 11.7 mmol) was added. Upon vigorously stirring for 10 minutes, a uniform reddish brown solution formed from a granular dispersion of the Br$_2$.

Activated MnO$_2$ (3.0 g, 29.3 mmol) was added, and after stirring for 10 minutes until a uniform suspension formed, 2,3,4-trifluorobenzoic acid (5.00 g, 28.4 mmol) was added. The reaction mixture was warmed from room temperature to 55° C. and stirred. While confirming the reaction progress, activated MnO$_2$ (3.00 g, 29.3 mmol) and Br$_2$ (0.60 mL, 11.7 mmol) were added after 3 hours, activated MnO$_2$ (1.30 g, 12.7 mmol) and Br$_2$ (0.30 mL, 5.86 mmol) were added after 8 hours, Br$_2$ (0.25 mL, 4.88 mmol) was added after 24 hours, and then the internal temperature was raised to 60° C.

Next, activated MnO$_2$ (3.05 g, 29.8 mmol) was added after 3 hours, activated MnO$_2$ (4.30 g, 42.0 mmol) and Br$_2$ (0.80 mL, 15.6 mmol) were added after 6 hours, activated MnO$_2$ (2.35 g, 23.0 mmol) and Br$_2$ (0.30 mL, 5.86 mmol) were added after 26 hours, and activated MnO$_2$ (3.20 g, 31.3 mmol) and Br$_2$ (0.40 mL, 7.81 mmol) were added after 59 hours (in total, 20.2 g (197 mmol, 7.0 eq) of activated MnO$_2$ and 3.25 mL (63.4 mmol, 2.2 eq) of Br$_2$). This was followed by stirring for 18 hours, and loss of the raw material was confirmed.

The reaction solution (orange suspension) was poured into ice (80 g). The obtained mixture was extracted with methylene chloride (100 mL×3). The organic layers were combined and rinsed with a 0.2N Na$_2$SO$_3$ aqueous solution (100 mL×2) and water (100 mL×6), and then dried over sodium sulfate and concentrated under reduced pressure to yield 2,3,4-trifluoro-5-bromobenzoic acid (4.53 g, 63%, purity: 98.2 LC area % (UV peak area % in LC)) as light brown, fine needle crystals.

The $^1$H-NMR data for the obtained 2,3,4-trifluoro-5-bromobenzoic acid are as follows.

$^1$H-NMR (CDCl$_3$, 270 MHz) δ (ppm): 8.07 (1H, ddd, J=7.1, 7.1, 2.6 Hz).

$^1$H-NMR (DMSO-d$_6$, 270 MHz) δ (ppm): 13.97 (br.s), 8.02-7.95 (1H, m).

The $^1$H-NMR data obtained using DMSO-d$_6$ was consistent with the $^1$H-NMR data (shown below) for the same compound described in International Patent Publication No. WO 99/01426 (Example 2, (a)).

$^1$H-NMR (DMSO-d$_6$, 400 MHz) δ (ppm): 13.97 (1H, br.s), 8.00-7.96 (1H, m).

Figure 2:
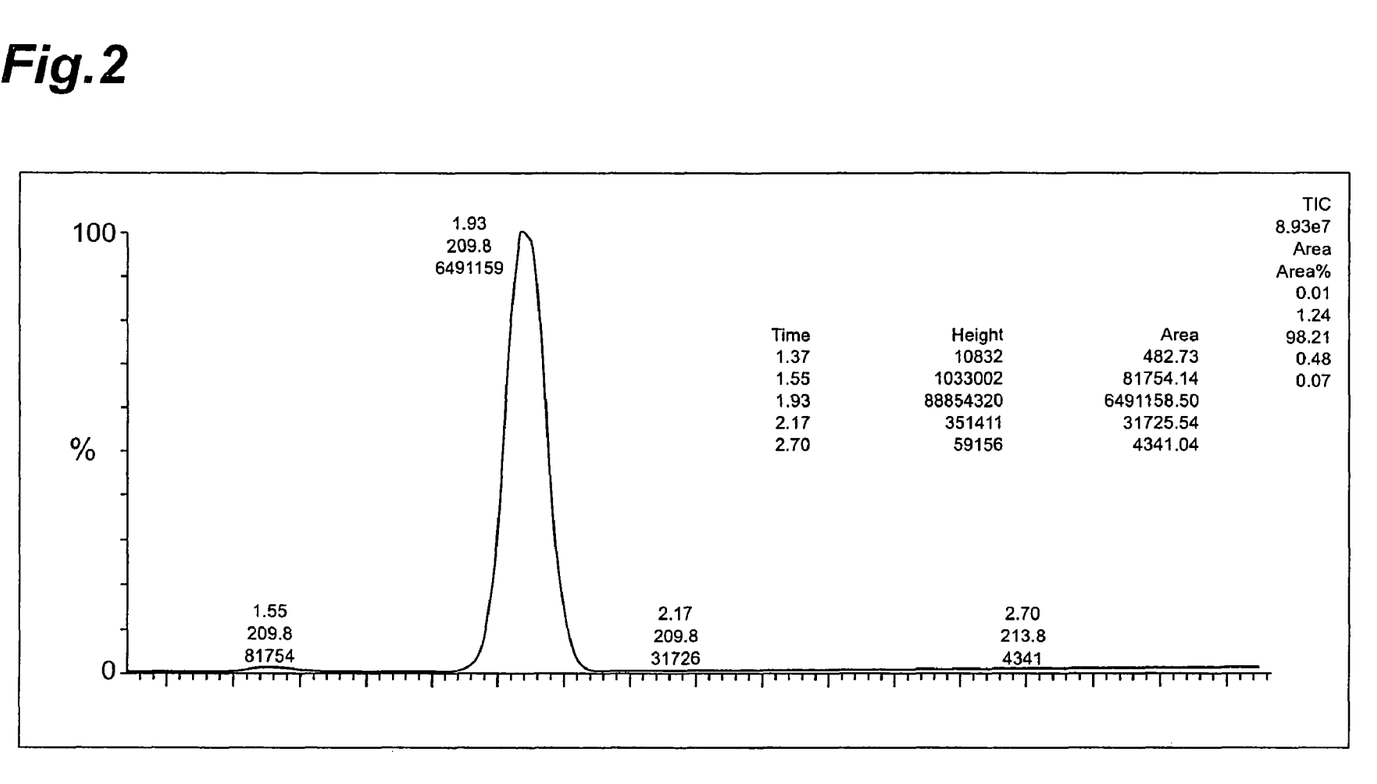
FIG. 2 is a chart from high performance liquid chromatography (HPLC) of the 2,3,4-trifluoro-5-bromobenzoic acid obtained in Example 2.

A chart from high performance liquid chromatography (HPLC) of the obtained 2,3,4-trifluoro-5-bromobenzoic acid is shown in FIG. 2. As seen in FIG. 2, the UV intensity of the target compound at 1.93 minutes was 98.21%, and there were four impurities with peak intensities (0.01% at 1.37 minutes, 1.24% at 1.55 minutes, 0.48% at 2.17 minutes, and 0.07% at 2.70 minutes). These results demonstrate that the production process of the invention yields 2,3,4-trifluoro-5-bromobenzoic acid in remarkably high purity and with remarkably high regioselectivity.

Example 3

2,3,4-Trifluoro-5-bromobenzoic Acid 2,3,4-trifluorobenzoic acid (10.0 g, 56.8 mmol), sodium bromate (34.0 g, 227.1 mmol), potassium sulfate (692 mg, 3.98 mmol) and 68 mL of water were added in that order into a three-necked flask equipped with a reflux apparatus, and then the mixture was thoroughly stirred to prepare a suspension. The reaction solution (suspension) was heated to an internal temperature of 90° C. in an oil bath. Next, H$_2$SO$_4$ (54 mL) was added dropwise over a period of more than 1 hour while controlling the dropping speed so that the internal temperature did not exceed 90° C.

Upon completion of the dropwise addition, the mixture was stirred at 90° C. for 1 hour. The oil bath was then removed and the reaction mixture was returned to room temperature, and then water (200 mL) was poured in. The product was obtained as insoluble matter, and was therefore separated by suction filtration. The obtained solid was rinsed with a small amount of cold water, and dried under reduced pressure to yield 7.75 g (53%) of 2,3,4-trifluoro-5-bromobenzoic acid as pale yellow needle crystals.

The $^1$H-NMR data for the obtained 2,3,4-trifluoro-5-bromobenzoic acid is shown below. Impurities (including regioisomers) were not observed by the $^1$H-NMR, and the largest impurity was <1%.

$^1$H-NMR (CD$_3$OD, 270 MHz) δ (ppm): 8.02 (1H, ddd, J=7.1, 7.1, 2.7 Hz).

Figure 3:
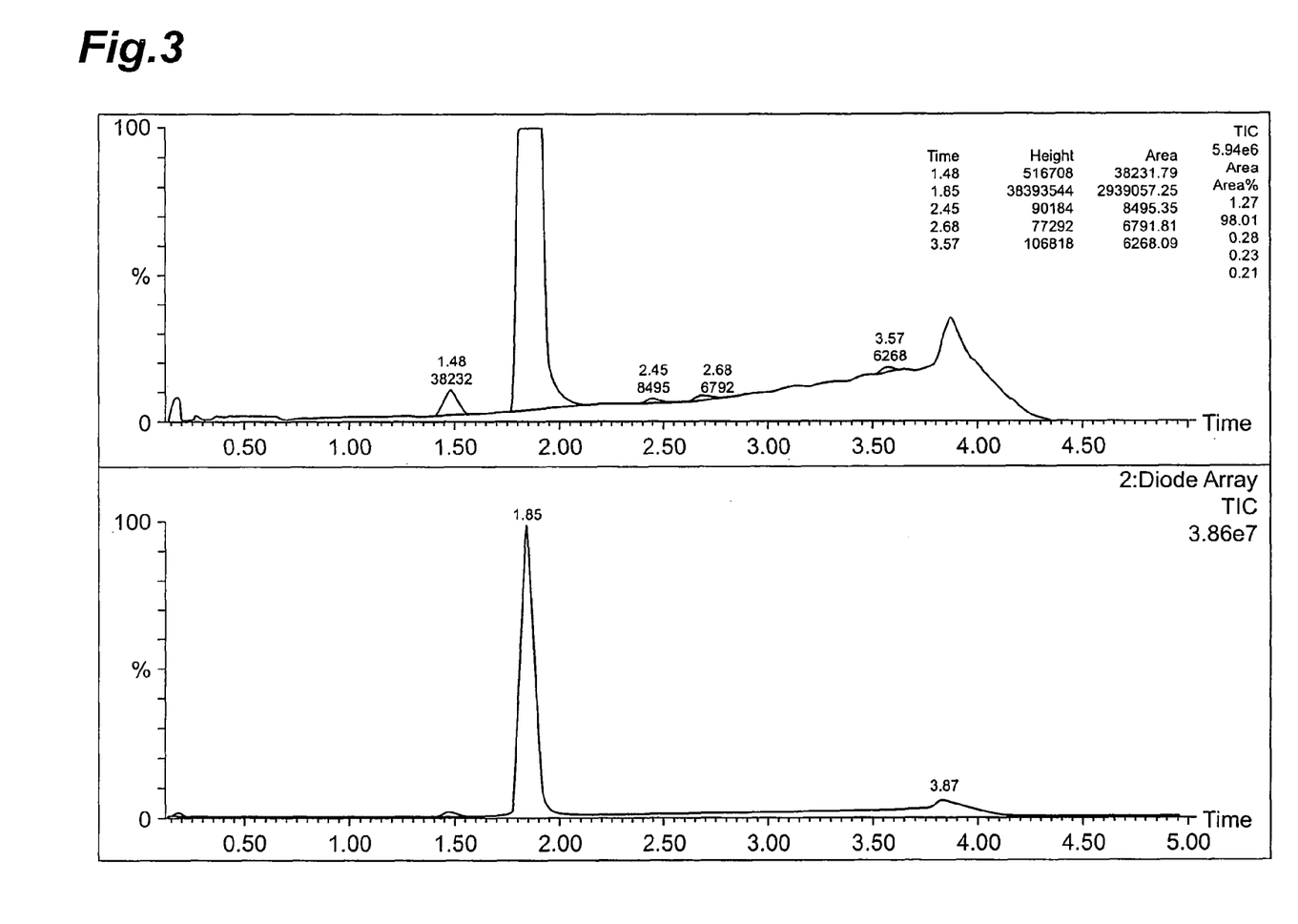
FIG. 3 is a chart from high performance liquid chromatography (HPLC) of the 2,3,4-trifluoro-5-bromobenzoic acid obtained in Example 3.

A chart from high performance liquid chromatography (HPLC) of the obtained 2,3,4-trifluoro-5-bromobenzoic acid is shown in FIG. 3. As seen in FIG. 3, the UV intensity of the target compound at 1.85 minutes was 98.01%, and there were four impurities with peak intensities (1.27% at 1.27 minutes, 0.28% at 2.45 minutes, 0.23% at 2.68 minutes, and 0.21% at 3.57 minutes). These results demonstrate that the production process of the invention yields 2,3,4-trifluoro-5-bromobenzoic acid in remarkably high purity and with remarkably high regioselectivity.

INDUSTRIAL APPLICABILITY

2,3,4-trifluoro-5-(iodo or bromo)benzoic acid, which is obtained by the production process of the invention, can be used as, for example, a raw material for production of 3,4-difluoro-2-(2-fluoro-4-iodophenylamino)-5-(formyl or vinyl)benzoic acid, 5-(formyl or vinyl)-3,4-difluoro-2-(4-iodo-2-methylphenylamino)benzoic acid and the like, which are synthetic intermediates of phenylaminobenzhydroxamic acid derivatives that are useful as drugs, especially as anti-cancer agents. The production process of the invention can be utilized for industrial production of 2,3,4-trifluoro-5-(iodo or bromo)benzoic acid.

The invention claimed is:

1. A process for production of 2,3,4-trifluoro-5-(iodo or bromo)benzoic acid represented by general formula (I)

below, the process comprising a halogenation step in which direct iodination or bromination of the 5-position of 2,3,4-trifluorobenzoic acid represented by formula (II) below is performed with an iodinating agent or brominating agent in a reaction solvent in the presence of an oxidizing agent, Chemical Formula 1

(I)

(II)

wherein X represents an iodine atom or bromine atom; and the reaction solvent contains an inorganic protonic acid and/or organic acid.

2. The process according to claim 1, wherein at least a portion of the inorganic protonic acids is sulfuric acid.

3. The process according to claim 1, wherein at least a portion of the organic acids is acetic acid.

4. The process according to claim 1, wherein the iodination or bromination is carried out in the copresence of an acid anhydride.

5. The process according to claim 4, wherein the acid anhydride is a carboxylic anhydride or sulfonic anhydride.

6. The process according to claim 4, wherein the acid anhydride is at least one selected from the group consisting of acetic anhydride, oxalic anhydride and maleic anhydride.

7. The process according to claim 1, wherein the oxidizing agent is a metal oxide.

8. The process according to claim 7, wherein the metal oxide is a Mn oxide and/or Cr oxide.

9. The process according to claim 1, wherein the oxide is activated $MnO_2$ and/or a $MnO_4^-$ salt.

10. The process according to claim 1, wherein the iodinating agent is $I_2$, and the brominating agent is $Br_2$.

11. The process according to claim 1, wherein the iodinating agent is a compound containing iodide anion, and the brominating agent is a compound containing bromide anion.

12. The process according to claim 1, wherein at least a portion of the iodinating agents and at least a portion of the brominating agents are an oxidizing agent.

13. The process according to claim 12, wherein
the iodinating agent that is also an oxidizing agent is at least one selected from the group consisting of $NaIO_3$, $NaIO_4$, $KIO_3$ and $KIO_4$, and
the brominating agent that is also an oxidizing agent is at least one selected from the group consisting of $NaBrO_3$, $NaBrO_4$, $KBrO_3$ and $KBrO_4$.

14. The process according to claim 1, wherein
the reaction solvent contains an inorganic protonic acid and/or organic acid, and
at least steps (a) and (b) below are carried out in the halogenation step,
(a) A step of adding the oxidizing agent and iodinating agent or the oxidizing agent and brominating agent to a mixture of the reaction solvent and an acid anhydride and
(b) A step of adding 2,3,4-trifluorobenzoic acid represented by formula (II) to the mixture obtained from step (a).

15. The process according to claim 14, wherein steps (a) and (b) are followed by step (c) below in the halogenation step,
(c) A step of adding the oxidizing agent and iodinating agent or the oxidizing agent and brominating agent to the mixture obtained from step (b).

16. The process according to any one of claim 1, comprising, after the halogenation step, an extraction step in which the reaction mixture obtained from the halogenation step is added to water, and 2,3,4-trifluoro-5-(iodo or bromo)benzoic acid represented by general formula (I) is then extracted with an organic solvent.

17. The process according to claim 1, wherein 2,3,4-trifluoro-5-(iodo or bromo)benzoic acid represented by general formula (I) is obtained at a purity of 98% or greater without purification after the halogenation step.

* * * * *